(12) United States Patent
Schmidt

(10) Patent No.: US 10,286,172 B1
(45) Date of Patent: May 14, 2019

(54) EPIGLOTTIS AVOIDANCE AIRWAY

(71) Applicant: Kevin Schmidt, Oak Brook, IL (US)

(72) Inventor: Kevin Schmidt, Oak Brook, IL (US)

( * ) Notice: Subject to any disclaimer, the term of this patent is extended or adjusted under 35 U.S.C. 154(b) by 0 days.

(21) Appl. No.: 16/026,387

(22) Filed: Jul. 3, 2018

Related U.S. Application Data

(60) Provisional application No. 62/630,572, filed on Feb. 14, 2018.

(51) Int. Cl.
*A61M 16/04* (2006.01)

(52) U.S. Cl.
CPC ........ *A61M 16/0488* (2013.01); *A61M 16/04* (2013.01); *A61M 16/0402* (2014.02); *A61M 16/0431* (2014.02); *A61M 16/0475* (2014.02); *A61M 16/0486* (2014.02); *A61M 16/0465* (2013.01)

(58) Field of Classification Search
CPC .. A61M 16/00; A61M 16/0048; A61M 16/04; A61M 16/0402; A61M 16/0415; A61M 16/0431; A61M 16/0475; A61M 16/0486; A61M 16/0488; A61M 16/049; A61M 16/0493; A61M 16/0495; A61M 16/0497

USPC ............................................. 128/860, 207.14
See application file for complete search history.

(56) References Cited

U.S. PATENT DOCUMENTS

| | | |
|---|---|---|
| 3,930,507 A | 1/1976 | Berman |
| 4,054,135 A | 10/1977 | Berman |
| 4,067,331 A | 1/1978 | Berman |
| 4,338,930 A | 7/1982 | Williams |
| 5,024,218 A | 6/1991 | Ovassapian et al. |
| 6,196,224 B1 * | 3/2001 | Alfery ............... A61M 16/0488 128/200.26 |
| 2007/0163596 A1 * | 7/2007 | Mikkaichi ............. A61M 16/04 128/207.14 |
| 2011/0297159 A1 * | 12/2011 | Meyer ................... A61B 5/097 128/207.14 |

* cited by examiner

*Primary Examiner* — Colin W Stuart

(74) *Attorney, Agent, or Firm* — MacMillan, Sobanski & Todd, LLC

(57) ABSTRACT

An oral airway includes a tubular body having a first end and a second end, and defining a first portion of an air flow channel, and a leg extending outwardly from the first end of the body, the leg defining a second portion of the air flow channel.

4 Claims, 8 Drawing Sheets

EPIGLOTTIS AVOIDANCE AIRWAY

CROSS-REFERENCE TO RELATED APPLICATIONS

This application claims the benefit of U.S. Provisional Application No. 62/630,572, filed Feb. 14, 2018, the disclosure of which is incorporated herein by reference.

BACKGROUND OF THE INVENTION

This invention relates in general to an improved supraglottic device for airway management. In particular, this invention relates to an improved structure for such a supraglottic device that is easier to insert into a patient and is more readily tolerated by a conscious or unconscious patient when in inserted in the patient's mouth and airway.

Airway management generally includes a set of maneuvers and medical procedures performed to prevent and relieve airway obstruction. This ensures an open pathway for air exchange between a patient's lungs and the atmosphere. This may be accomplished by either clearing a previously obstructed airway, or by preventing airway obstruction in cases such as anaphylaxis, an obtunded patient, or medical sedation. Airway obstruction can be caused by the tongue, foreign objects, the tissues of the airway itself, and bodily fluids such as blood and gastric contents, i.e., aspiration.

Airway management is commonly divided into two categories: basic and advanced. Basic techniques are generally non-invasive and do not require specialized medical equipment or advanced training. These include head and neck maneuvers to optimize ventilation, abdominal thrusts, and back blows.

Advanced airway management techniques require specialized medical training and equipment, and may be further categorized anatomically into supraglottic devices, such as oropharyngeal and nasopharyngeal airways, infraglottic techniques, such as tracheal intubation, and surgical methods, such as cricothyrotomy, and tracheotomy.

Artificial airways include endotracheal tubes, laryngeal mask airways, and oral airways. Known endotracheal tubes are configured to pass through the nose or mouth between the vocal cords and into the trachea. This placement is beneficial in patients suffering from respiratory insufficiency and coma as well as many patients under general anesthesia. A laryngeal mask airway is configured to pass through the mouth and cover and surround the larynx during general anesthesia, but typically is not tolerated by a patient while awake.

Typical oral airways are configured to pass over and past the tongue in the midline to hold the tongue forward. Oral airways may be placed in cardiac arrest patients to temporarily open the airway if it is obstructed prior to the placement of an endotracheal tube. Anesthesia providers often place an oral airway in heavily sedated patients to keep the airway open, or in patients who are recuperating from anesthesia in recovery room, but become more sedated after narcotics are given to control post operative pain, and thus may lose their airway.

One known oral airway is an oropharyngeal airway, also known as a Guedel pattern airway that is used to maintain or open a patient's airway. The oropharyngeal airway does this by preventing the tongue from covering the epiglottis, which could prevent the person from breathing. When a person becomes unconscious, the muscles in their jaw may relax and allow the tongue to obstruct the airway.

Artificial airways are instrumental in maintaining open airways in many groups of patients including surgical patients, comatose patients, and patients with sleep apnea. Any loss of an open airway may result in low oxygen levels and high carbon dioxide levels which may lead to cardiovascular compromise, myocardial infarction, brain damage, and death. The loss of an airway for as little as a few minutes, even in a healthy person, may rapidly lead to irreversible brain damage or death.

Sleep apnea is becoming a wide spread health problem affecting nearly 25% of the adult population, and which may lead to inability to concentrate, hypertension, daytime somnolence, type 2 diabetes, increased incidence of accidents at work and by automobile, and in the worst case, stroke and cardiac failure.

The industry standard oral airways are very poorly tolerated in an awake patient because of the shape and location of a properly placed airway, and because of the negative reaction of the oral and pharyngeal structures to any pressure or stimulation. A typical oral airway may therefore lead to coughing, retching, vomiting, and excessive salivation, and can lead to bronchospasm, which is similar to an asthma attack, and laryngospasm, which is an involuntary closure of the vocal cords that may lead rapidly to cardiac arrest in children.

Disadvantageously, placement of the oral airway may also push the base of the tongue over the airway closing it off, and worsening the airway obstruction.

During sedation anesthesia, also called twilight sleep, even with continuous infusions of sedatives, the depth of sedation and the stimulation of surgery varies. With a current industry standard oral airway in place, an increase in surgical stimulation or a decrease in sedation level and movement of the airway near the epiglottis may lead to sudden explosive coughing, breath holding, valsalva, i.e., bearing down which may increase blood pressure and venous pressure and which may cause bleeding into the tissues, struggles to secure the airway, risks to maintaining the sterile surgical field, and delays in completing surgery.

Thus, it would be desirable to provide an improved structure for a supraglottic device that is easier to insert into a patient and is more readily tolerated by a conscious or unconscious patient when in inserted in the patient's mouth and airway.

SUMMARY OF THE INVENTION

This invention relates to an improved structure for a supraglottic device that that is easier to insert into a patient, avoids the epiglottis, and is more readily tolerated by a conscious or unconscious patient when in inserted in the patient's mouth and airway. The supraglottic device is configured as an oral airway that is configured to avoid the epiglottis and includes a tubular body having a first end and a second end, and defining a first portion of an air flow channel, and a leg extending outwardly from the first end of the body, the leg defining a second portion of the air flow channel.

Various aspects of this invention will become apparent to those skilled in the art from the following detailed description of the preferred embodiment, when read in light of the accompanying drawings.

DETAILED DESCRIPTION OF THE PREFERRED EMBODIMENT

Figure 1:
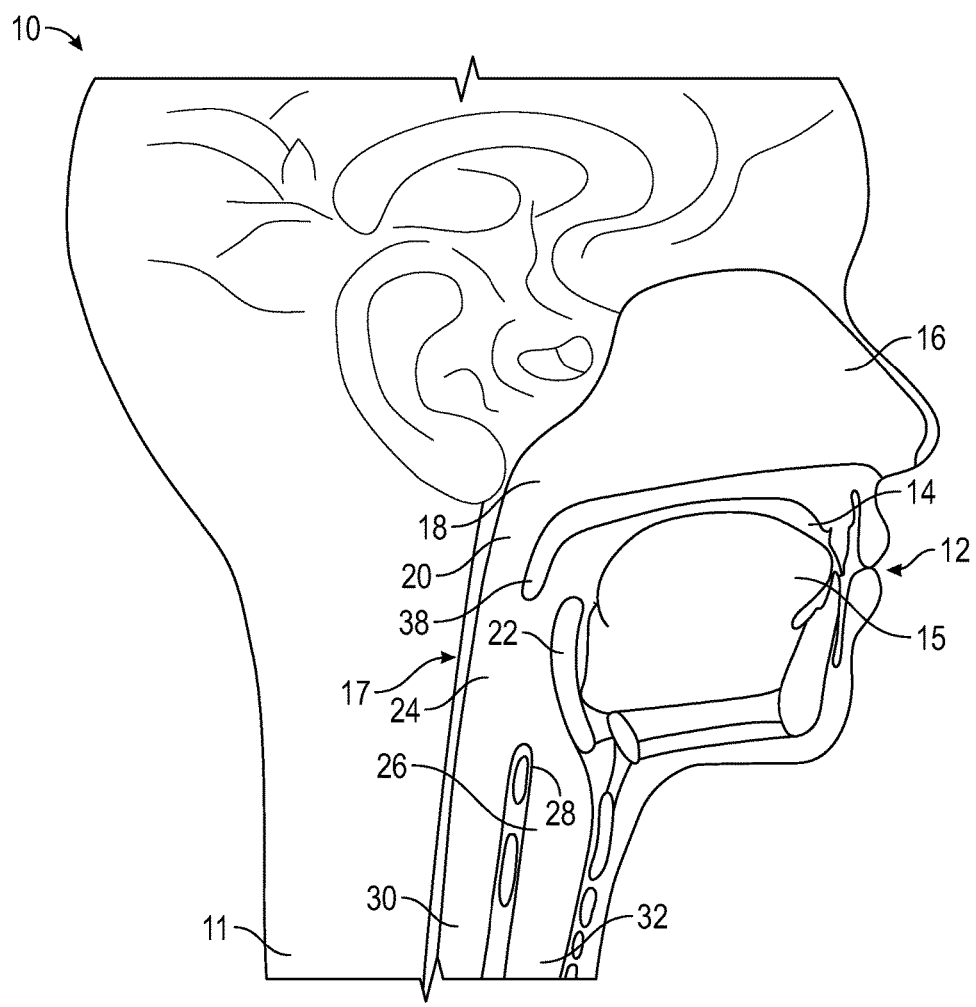
FIG. 1 is a cross sectional side view of the anatomic structures of the head and neck.

FIG. 1 is a cross sectional side view of anatomic structures of a head 10 and neck 11 of a typical human patient in a normal breathing position. The anatomic structures illustrated in FIG. 1 include the mouth 12, the oral cavity 14, the tongue 15, the nasal cavity 16, the pharynx 17, comprising the nasopharynx 18, the oropharynx 20, and the hypopharynx 24, the epiglottis 22, the larynx 26, the posterior wall 28 of the larynx 26, the esophagus 30, the trachea 32, and the uvula 38.

Figure 2:
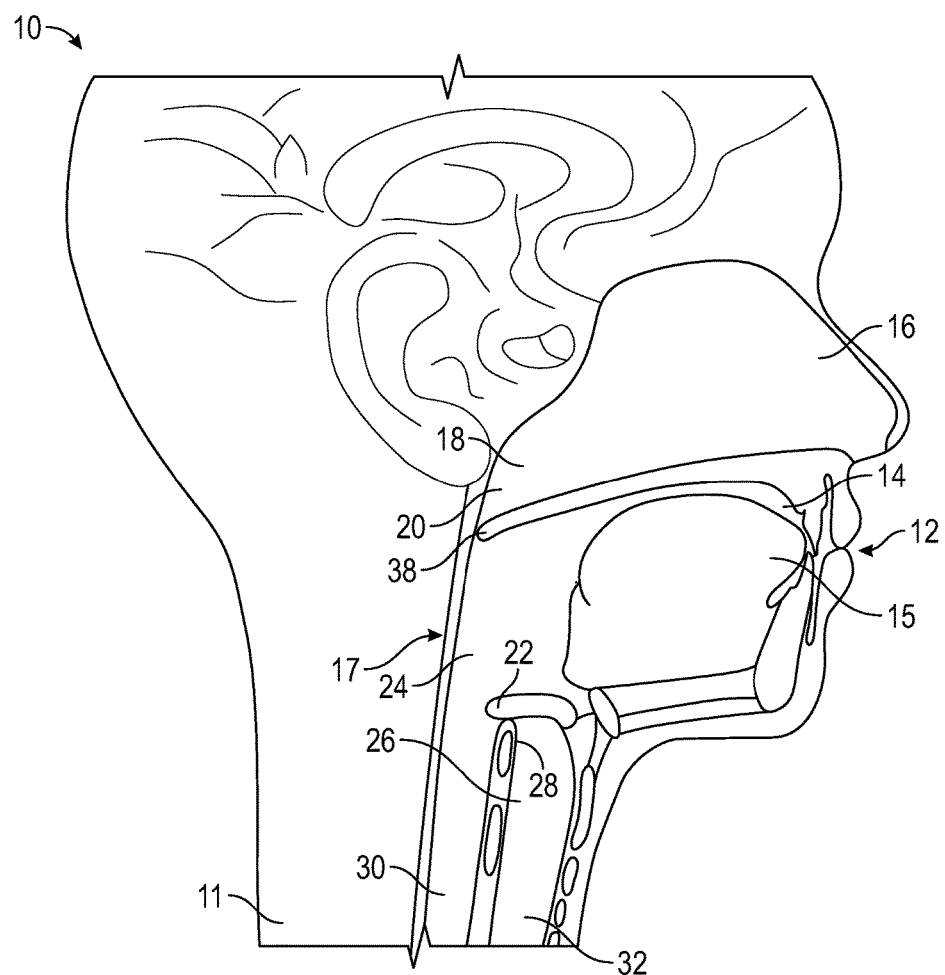
FIG. 2 is a first alternate cross sectional side view of the anatomic structures of the head and neck illustrated in FIG. 1 showing the epiglottis and the uvula in a swallowing position.

FIG. 2 is a cross sectional side view of the anatomic structures of the head 10 and neck 11 illustrated in FIG. 1, but shows the epiglottis 22 and the uvula 38 in a normal swallowing position.

Figure 3:
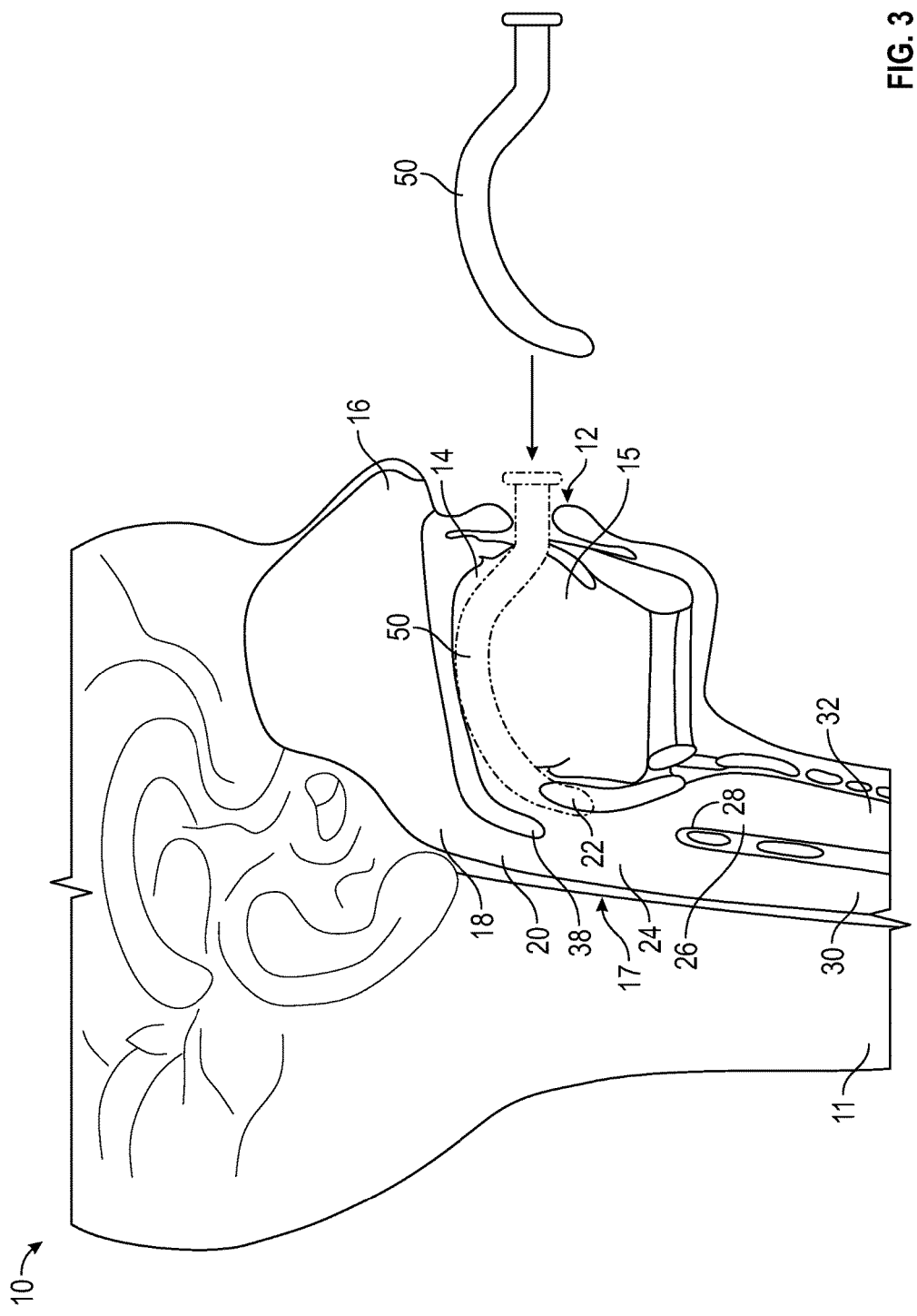
FIG. 3 is a second alternate cross sectional side view of the anatomic structures of the head and neck illustrated in FIG. 1 showing a first embodiment of the improved epiglottis avoidance airway according to this invention inserted into the mouth and airway.

FIG. 3 is a cross sectional side view of the anatomic structures of the head 10 and neck 11 illustrated in FIGS. 1 and 2, but shows a first embodiment of an epiglottis avoidance airway 50 according to this invention before and after insertion into the mouth 12 and pharynx 17.

Figure 4:
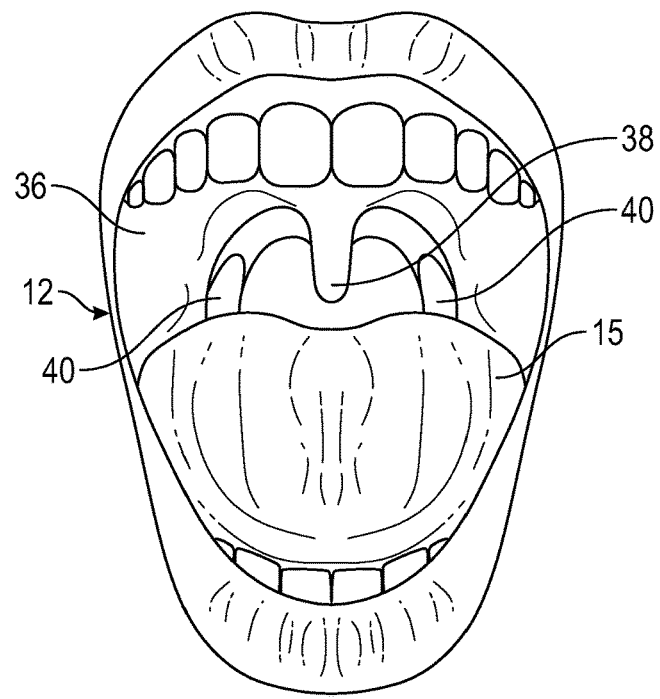
FIG. 4 is a schematic open mouth view of the head illustrated in FIGS. 1 through 3 showing the uvula, soft palate, and tongue.
Figure 5:
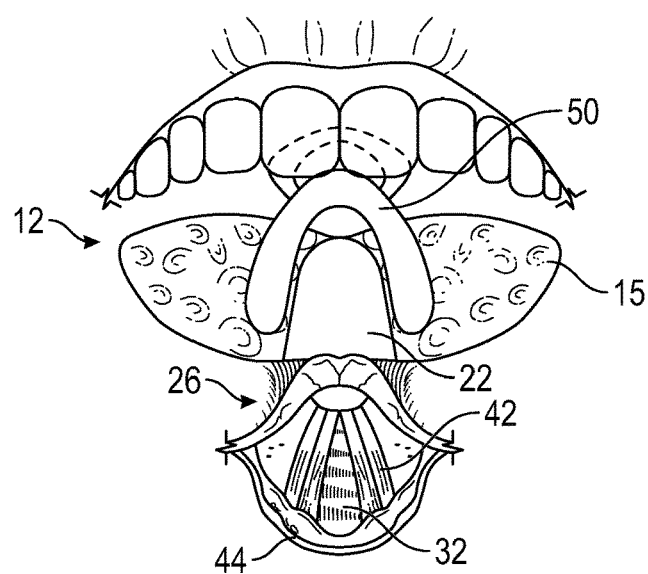
FIG. 5 is a schematic view of the interior of the mouth illustrated in FIG. 1, viewed from back to front, and showing the larynx and surrounding tissues, the epiglottis, the tongue, and the vocal cords.

In FIG. 4, the mouth 12 is shown in an open position to illustrate the tongue 15, the soft palate 36, the uvula 38, and the tonsils 40. FIG. 5 illustrates the mouth 12 when viewed from a back to a front thereof with the epiglottis avoidance airway 50 positioned therein, and provides a schematic view of the interior of the larynx 26 and the tissues surrounding the larynx 26, including the tongue 15, the epiglottis 22, the trachea 32, the vocal cords 42. The corniculate cartilage 44 is also shown.

Referring again to the drawings, the first embodiment of the epiglottis avoidance airway according to this invention is illustrated generally at 50 in FIGS. 6 through 10.

The epiglottis avoidance airway 50 has a first or distal end 50A and a second or proximal end 50B, and includes an elongated tubular body 52 having a first end 52A and a second end 52B, and defining a first channel portion 56 of an air flow channel 57. A circumferentially extending flange 54 is formed at the second end 52B of the body 52 and defines an opening to the first channel portion 56 of the air flow channel 57. A first or inwardly facing surface 58 of the flange 54 is configured to engage and rest against the mouth 12 of the patient.

Two elongated legs 60 extend outwardly from the first end 52A of the body 52. Distal ends of the legs 60 define pharyngeal tips of the legs 60. The legs 60 are arcuate in shape when viewed from the side (see FIGS. 8 and 9). The arcuate shape of the legs 60 conforms to the shape and natural angles of the airway, i.e., the mouth 12 and pharynx 17. The legs 60 are spaced apart by a space S, such that the space S defines an open area, the purpose for which is explained in detail below.

Figure 10:
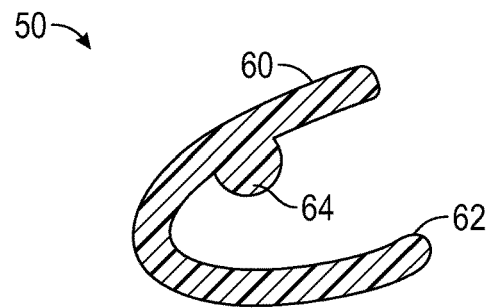
FIG. 10 is a cross-sectional view taken along the ling 10-10 in FIG. 7.

The legs 60 have a substantially C-shaped transverse section as shown in FIG. 10 and elongated and inwardly facing slots or openings 62 that define second channel portions 65 of the air flow channel 57. Although the legs 60 are illustrated as having a substantially C-shaped transverse section, the transverse section of the legs 60 may alternatively have any other desired shape, such as substantially V-shaped, or any other desired geometric or non-geometric shape in combination with the elongated and inwardly facing openings 62.

The legs 60 may be provided with raised portions, such as studs formed on an inside surface of the legs 60. An example of such a stud is shown at 64 in FIG. 10. The body 52 may also have raised portions formed on an inside surface of the body 52, such as a stud 66 best shown in FIGS. 6 and 7. Although illustrated as studs 64 and 66, the raised portions may alternatively be formed as elongated protrusions, such as ridges (not shown) extending outwardly from an inside surface of the body 52 and/or the legs 60. In the illustrated embodiment, two legs 60 are shown. It will be understood however, that if desired the epiglottis avoidance airway 50 may have only one leg 60.

In the illustrated embodiment, the epiglottis avoidance airway 50 is formed from polyethylene. Alternatively, the epiglottis avoidance airway 50 may be formed from any desired flexible or semi-flexible material, such as soft vinyl, latex, soft elastomer, plastic, and pliable resin, thus allowing the epiglottis avoidance airway 50 to be at least partially compressible. The combination of the material and the substantially C-shaped transverse section of the legs 60 allow the legs to be compressed while maintaining air flow therethrough. Additionally, the studs 64 and 66 or other raised portions (not shown) formed on the inside surfaces of the legs 60 and the body 52, respectively, facilitate airflow by preventing the legs 60 and the body 52 from completely closing if compressed.

In use, a medical professional may insert the distal end 50A of the epiglottis avoidance airway 50 into the patient's mouth 12 and pharynx 17 until the inwardly facing surface 58 of the flange 54 engages or is near the mouth 12 of the patient. Air, oxygen, or other gas may then be introduced into the patient through the first channel portion 56 of the air flow channel 57 and the second channel portion 65 of the airflow channel 57 of the epiglottis avoidance airway 50.

The distal ends or pharyngeal tips of the legs 60 are directed away from the midline on one or both sides of the mouth 12, and the epiglottis 22 and the base of the tongue 15 are subjected to less contact relative to a known oral airway. Thus, the risk of sudden coughing, retching, and vomiting are substantially and advantageously reduced. Because the leg or legs 60 of the epiglottis avoidance airway 50 are directed away from the midline, there is less chance that pushing the epiglottis avoidance airway 50 into the patient's mouth 12 and pharynx 17 will obstruct the patient's airway with the tongue 15 when compared to known oral airways.

The legs 60 are further configured such that they are directed away from midline structures and the epiglottis 22, thus providing more comfort to the patient than conventional airway devices. The epiglottis avoidance airway 50 is also easier to insert into a patient, avoids the epiglottis 17, and is more readily tolerated by a conscious or unconscious patient when in inserted in the patient's mouth 12 and pharynx 17.

Further, swallowing is a complex mechanism that involves sensory input from the soft palate 36, the uvula 38, and the tongue 15, and their contact with each other. Known oral airways separate and prevent contact between the structures, i.e., the soft palate 36, the uvula 38, and the tongue 15, making swallowing less effective, causing saliva to collect and pool near the larynx 26, and increasing the risk of aspiration of secretions or regurgitated gastric fluids.

Aspiration of fluids may lead to aspiration pneumonia, which has a significant risk of death, even in healthy patients. Advantageously, the space S between the legs 60 defines an open area at the level of the uvula 38, so that the tongue 15 can contact the uvula 38 and the soft palate 36, and thereby improve the effectiveness of swallowing. Effective swallowing and the clearance of secretions is also comforting to the patient, and allows the patient to avoid the choking sensation of fluid near the larynx 26 as may occur with known oral airways.

Figure 11:
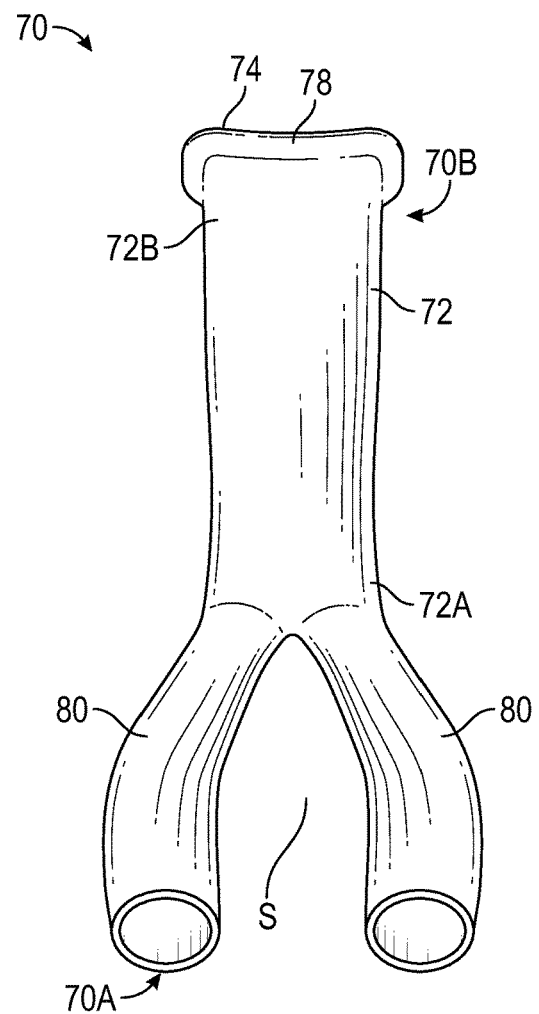
FIG. 11 is a perspective view of a lower surface of a second embodiment of the improved epiglottis avoidance airway according to this invention.

Referring now to FIG. 11, a second embodiment of the epiglottis avoidance airway according to this invention is illustrated generally at 70.

The epiglottis avoidance airway 70 is similar to the epiglottis avoidance airway 50 and has a first or distal end 70A and a second or proximal end 70B, and includes an elongated tubular body 72 having a first end 72A and a second end 72B. A circumferentially extending flange 74 is formed at the second end 72B of the body 52 and defines an air passageway therethrough. A first or inwardly facing surface 78 of the flange 74 is configured to engage and rest against the mouth 12 of the patient.

Figure 8:
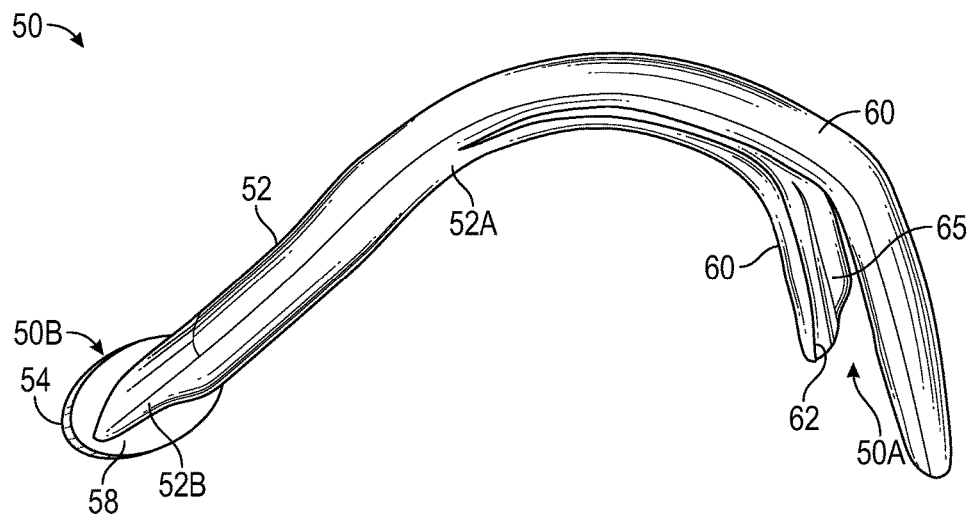
FIG. 8 is a perspective side elevational view of the epiglottis avoidance airway illustrated in FIGS. 3, and 5 through 7.
Figure 9:
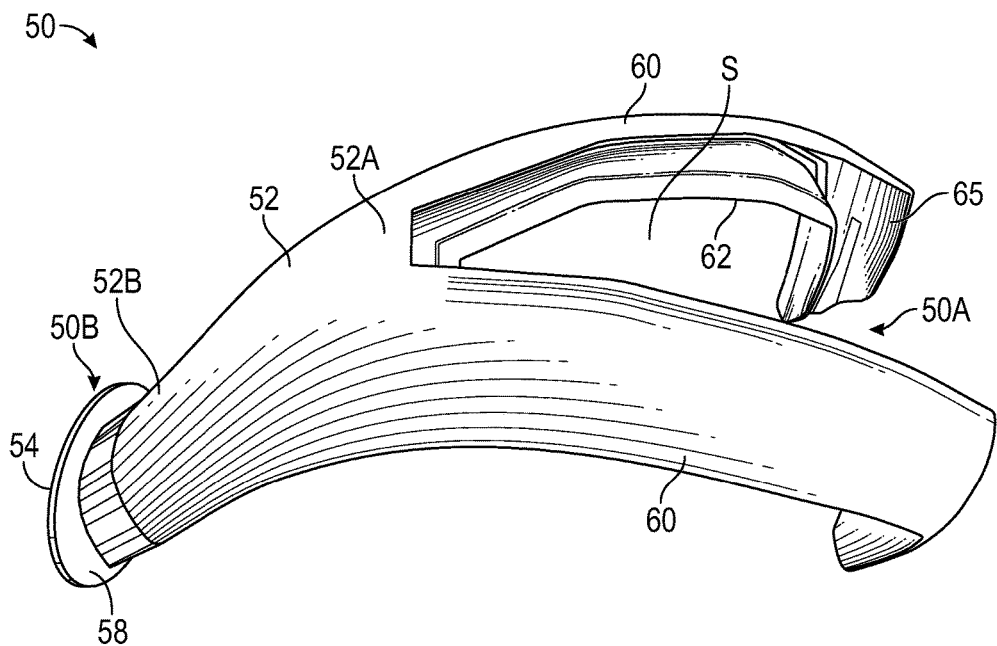
FIG. 9 is an alternate perspective view of the epiglottis avoidance airway illustrated in FIGS. 3, and 5 through 8 showing an interior channel of a leg.

Two elongated legs 80 extend outwardly from the first end 72A of the body 72. Like the legs 60, the legs 80 are arcuate in shape when viewed from the side, and thus have a shape similar to the legs 60 as shown in FIGS. 8 and 9. The arcuate shape of the legs 80 conforms to the shape and natural angles of the airway, i.e., the mouth 12 and pharynx 17.

The legs 80 are tubular and have a substantially circular transverse section. Alternatively, the transverse section of the legs 80 may have any other desired shape, such as oval, or any other desired geometric or non-geometric shape.

Figure 6:
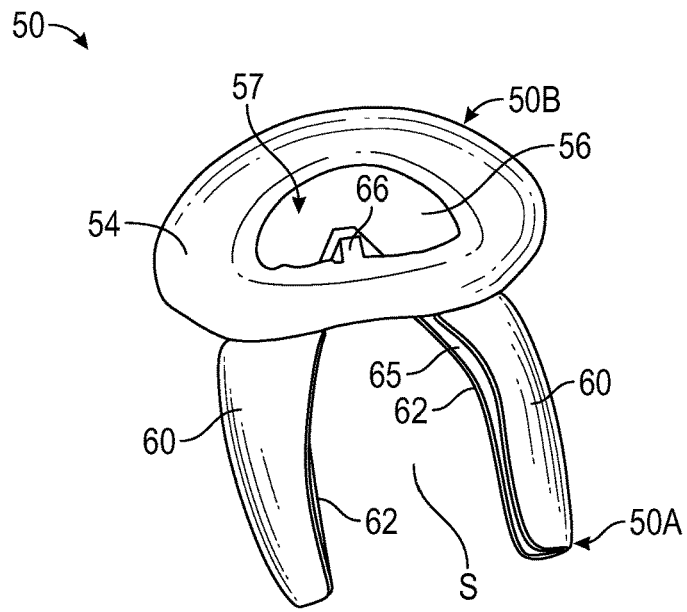
FIG. 6 is an end view of the proximal end of the first embodiment of the epiglottis avoidance airway according to this invention.
Figure 7:
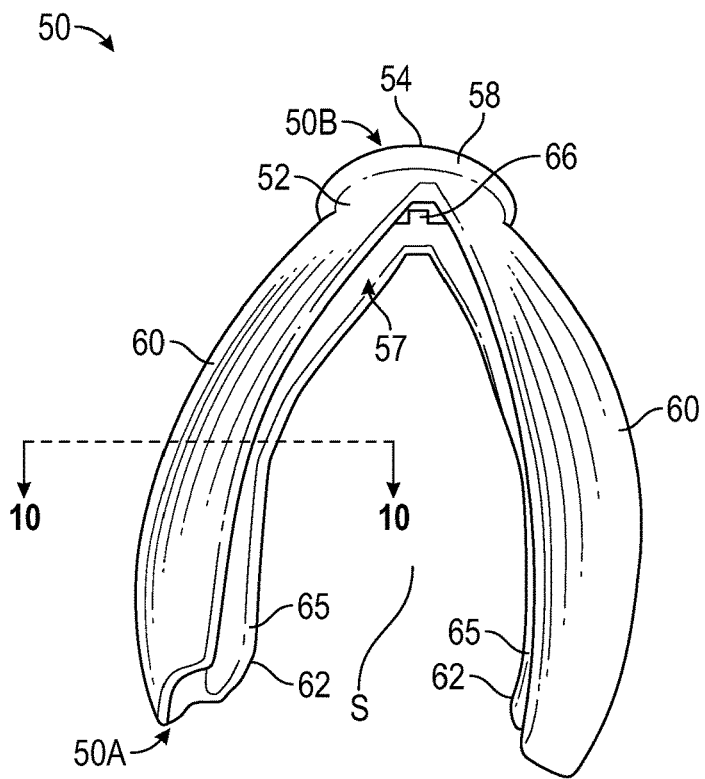
FIG. 7 is perspective view of an upper surface and a distal end of the epiglottis avoidance airway illustrated in FIGS. 3, 5, and 6.

Although not illustrated in FIG. 11, the legs 80 may be provided with raised portions, such as the studs 64 shown in FIG. 10 and the stud 66 shown in FIGS. 6 and 7. As described above, the studs 64 and 66 may alternatively be formed as elongated protrusions, such as ridges (not shown) extending outwardly from an inside surface of the body 72 and/or the legs 80.

Like the epiglottis avoidance airway 50, the epiglottis avoidance airway 70 is formed from polyethylene. Alternatively, the epiglottis avoidance airway 70 may be formed from any desired flexible or semi-flexible material, such as soft vinyl, latex, soft elastomer, plastic, and pliable resin, thus allowing the epiglottis avoidance airway 70 to be at least partially compressible. The studs 64 and 66 or other raised portions (not shown in FIG. 11) formed on the inside surfaces of the legs 80 and the body 72, respectively, facilitate airflow by preventing the legs 80 and the body 72 from completely closing if compressed.

Figure 12:
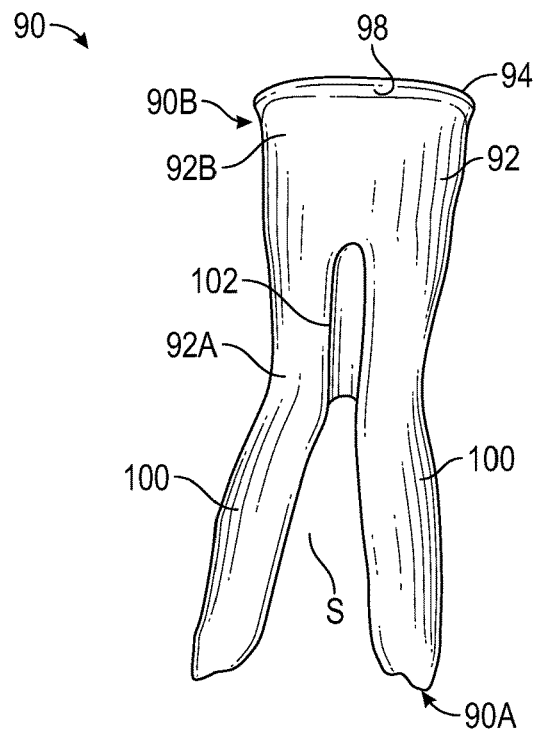
FIG. 12 is a perspective view of a lower surface of a third embodiment of the improved epiglottis avoidance airway according to this invention.
Figure 13:
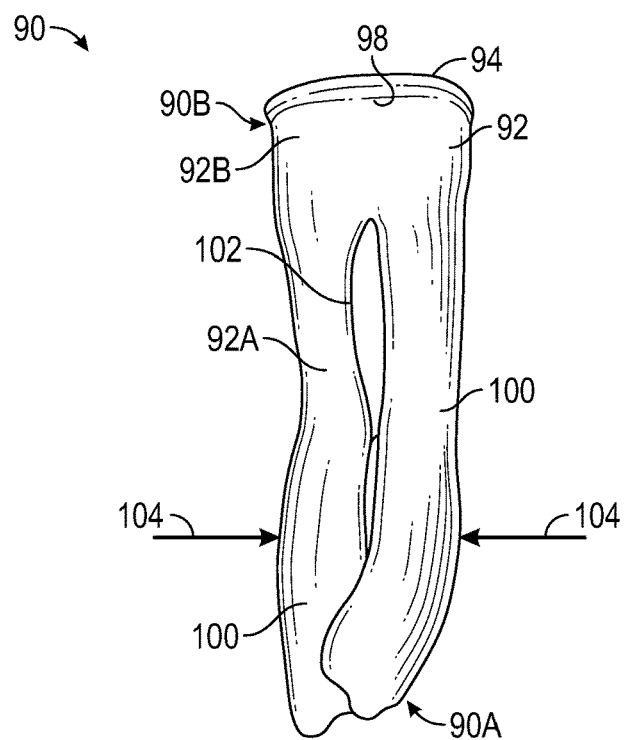
FIG. 13 is a perspective view of the improved epiglottis avoidance airway illustrated in FIG. 12 showing the legs compressed for insertion into the mouth and airway.

Referring now to FIGS. 12 and 13, a third embodiment of the epiglottis avoidance airway according to this invention is illustrated generally at 90.

The epiglottis avoidance airway 90 is substantially similar to the epiglottis avoidance airway 50 and has a first or distal end 90A and a second or proximal end 90B, and includes an elongated tubular body 92 having a first end 92A and a second end 92B. A circumferentially extending flange 94 is formed at the second end 92B of the body 92 and defines an air passageway therethrough. A first or inwardly facing surface 98 of the flange 94 is configured to engage and rest against the mouth 12 of the patient.

Two elongated legs 100 extend outwardly from the first end 92A of the body 92. Like the legs 60, the legs 100 are arcuate in shape when viewed from the side, and thus have a shape similar to the legs 60 as shown in FIGS. 8 and 9. The arcuate shape of the legs 100 conforms to the shape and natural angles of the airway, i.e., the mouth 12 and pharynx 17. The legs 100 are substantially the same as the legs 60, have the substantially C-shaped transverse section and the elongated and inwardly facing openings 62 that define the second channel portions 65 of the air flow channel 57 as shown in FIG. 10 (not shown in FIGS. 12 and 13). As described above, the transverse section of the legs 100 may alternatively have any other desired shape, such as substantially V-shaped, or any other desired geometric or non-geometric shape in combination with the elongated and inwardly facing openings 62.

Although not illustrated in FIGS. 12 and 13, the legs 100 may be provided with raised portions, such as the studs 64 shown in FIG. 10 and the stud 66 shown in FIGS. 6 and 7. As described above, the studs 64 and 66 may alternatively be formed as elongated protrusions, such as ridges (not shown) extending outwardly from an inside surface of the body 92 and/or the legs 100.

A compression slot 102 is formed in a lower surface of the body 92 (the downwardly or tongue 15 facing surface of the body 92 when viewing the epiglottis avoidance airway 90 inserted in the mouth 12, such as shown in FIG. 3). The compression slot 102 extends from the legs 100 at the first end 92A of the body 92 toward the second end 92B of the body 92.

Like the epiglottis avoidance airway 50, the epiglottis avoidance airway 90 is formed from polyethylene. Alternatively, the epiglottis avoidance airway 90 may be formed from any desired flexible or semi-flexible material, such as soft vinyl, latex, soft elastomer, plastic, and pliable resin, thus allowing the epiglottis avoidance airway 90 to be at least partially compressible. The studs 64 and 66 or other raised portions (not shown in FIGS. 12 and 13) formed on the inside surfaces of the legs 100 and the body 92, respectively, facilitate airflow by preventing the legs 100 and the body 92 from completely closing if compressed.

Advantageously, the compression slot 102 is configured to allow the legs 100 of epiglottis avoidance airway 90 to be compressed toward each other in response to a force in the direction of the arrows 104, such as applied by the medical professional inserting the epiglottis avoidance airway 90 (see FIG. 13). The compressed configuration of the epiglottis avoidance airway 90 shown in FIG. 13 allows the epiglottis avoidance airway 90 to be more easily inserted into the mouth 12 and pharynx 17.

The principle and mode of operation of this invention have been explained and illustrated in its preferred embodiment. However, it must be understood that this invention may be practiced otherwise than as specifically explained and illustrated without departing from its spirit or scope.

What is claimed is:

1. An oral airway comprising:
   a tubular body having a first end and a second end, and defining a first channel portion of an air flow channel;
   a first leg extending outwardly from the first end of the tubular body and including an elongated opening; and
   a second leg extending outwardly from the first end of the tubular body and including an elongated opening;
   wherein the elongated openings of the first leg and the second leg define a second channel portion of the air flow channel; and
   wherein the first leg and the second leg are spaced apart by a space that defines an open area, such that when the oral airway is fully inserted into a patient's mouth and pharynx, the space is positioned at the level of the uvula so that the patient's tongue may contact the uvula and the soft palate, thereby improving the effectiveness of swallowing.

2. The oral airway according to claim 1, further including a raised portion formed on an inside surface of each leg.

3. The oral airway according to claim 2, wherein the raised portion is a stud.

4. The oral airway according to claim 1, wherein the tubular body and the legs are compressible.

\* \* \* \* \*